(12) United States Patent
Hart

(10) Patent No.: US 12,185,947 B2
(45) Date of Patent: Jan. 7, 2025

(54) TECHNIQUES FOR CONTROLLING AN END EFFECTOR

(71) Applicant: INTUITIVE SURGICAL OPERATIONS, INC., Sunnyvale, CA (US)

(72) Inventor: J. Scot Hart, San Carlos, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 907 days.

(21) Appl. No.: 17/211,692

(22) Filed: Mar. 24, 2021

(65) Prior Publication Data

US 2021/0298751 A1 Sep. 30, 2021

Related U.S. Application Data

(60) Provisional application No. 63/000,300, filed on Mar. 26, 2020.

(51) Int. Cl.
*A61B 17/072* (2006.01)
*A61B 17/00* (2006.01)
*A61B 90/00* (2016.01)

(52) U.S. Cl.
CPC ............ *A61B 17/07207* (2013.01); *A61B 2017/00017* (2013.01); *A61B 2017/07257* (2013.01);
(Continued)

(58) Field of Classification Search
CPC ............ A61B 17/068; A61B 17/072; A61B 17/07207; A61B 2017/07257;
(Continued)

(56) References Cited

U.S. PATENT DOCUMENTS

2014/0200612 A1* 7/2014 Weir .................. A61B 90/98
227/176.1
2016/0270779 A1* 9/2016 Chaghaerdi ............ A61B 34/35
(Continued)

FOREIGN PATENT DOCUMENTS

| JP | 2022526258 | * | 5/2022 | ... A61B 2017/00017 |
| WO | WO-2017132611 A1 | * | 8/2017 | ....... A61B 17/00234 |
| WO | WO-2019043508 A2 | * | 3/2019 | ....... A61B 17/07207 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Stephen F. Gerrity
*Assistant Examiner* — Linda J Hodge
(74) *Attorney, Agent, or Firm* — Artegis Law Group, LLP

(57) ABSTRACT

Techniques for controlling an end effector include a computer-assisted device having a drive system configured to actuate a moveable element to a first commanded position and a control unit coupled to the drive system. The control unit is configured to actuate, using the drive system, the moveable element to the first commanded position. The control unit is further configured to monitor a force or torque applied by the drive system to actuate the moveable element to the first commanded position, determine a force or torque limit for the drive system based on the monitored force or torque applied by the drive system in response to determining that the moveable element has reached a first position, and further actuate the moveable element to a second commanded position while limiting a force or torque applied by the drive system based on the determined force or torque limit.

20 Claims, 4 Drawing Sheets

(52) U.S. Cl.
CPC ............ *A61B 2017/07278* (2013.01); *A61B 2017/07285* (2013.01); *A61B 2090/064* (2016.02); *A61B 2090/066* (2016.02)

(58) Field of Classification Search
CPC ........... A61B 2017/07278; A61B 2017/07285; A61B 2017/00017; A61B 2017/00022; A61B 2017/00039; A61B 2017/00075; A61B 2017/00137; A61B 2017/00367; A61B 2017/00398; A61B 2090/064; A61B 2090/066; A61B 2017/031; A61B 34/35; H02P 6/10
See application file for complete search history.

(56) References Cited

U.S. PATENT DOCUMENTS

| | | | |
|---|---|---|---|
| 2019/0059884 A1* | 2/2019 | Shelton, IV | ....... A61B 17/1155 |
| 2019/0183503 A1* | 6/2019 | Shelton, IV | ........... A61B 90/06 |
| 2023/0171304 A1* | 6/2023 | Shelton, IV | ......... A61B 5/0066 709/201 |

* cited by examiner

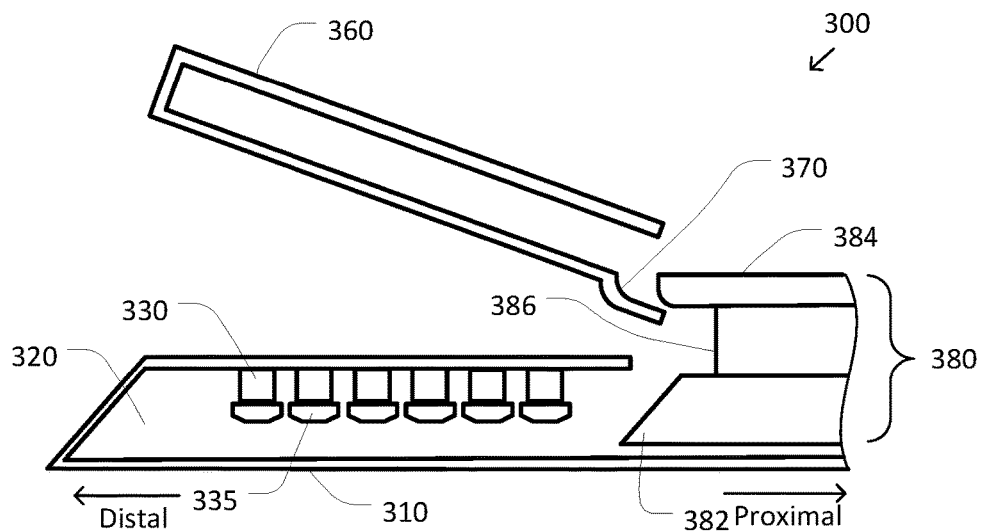
FIG. 3A
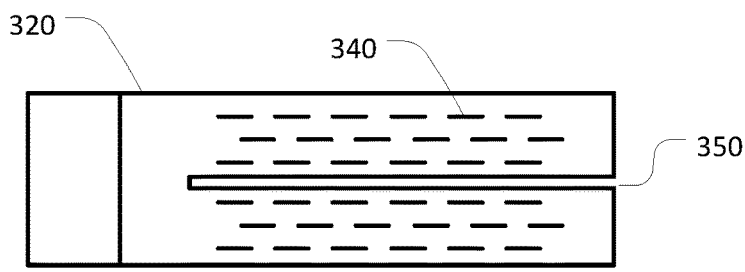
FIG. 3B
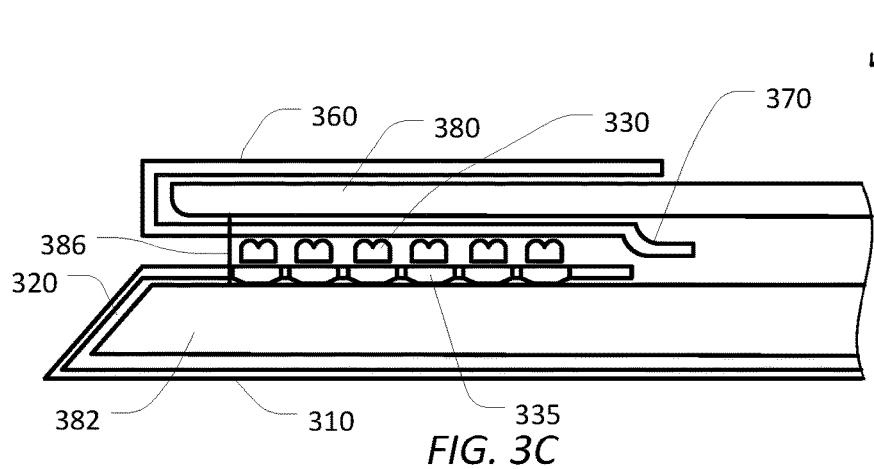 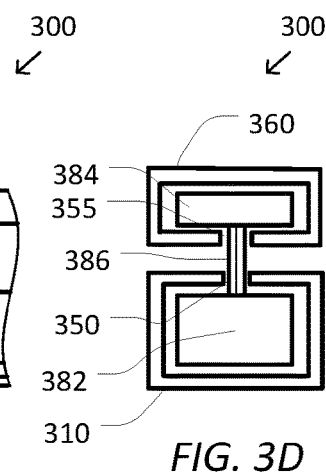
FIG. 3C  FIG. 3D

TECHNIQUES FOR CONTROLLING AN END EFFECTOR

CROSS-REFERENCE TO RELATED APPLICATIONS

The present application claims priority to U.S. Provisional Patent Application No. 63/000,300, filed Mar. 26, 2020 and titled "Techniques for Controlling an End Effector," the entire contents of which are hereby incorporated by reference.

TECHNICAL FIELD

The present disclosure relates generally to operation of devices with repositionable arms and end effectors and more particularly to operation of an end effector with a moveable element.

BACKGROUND

More and more devices are being replaced with computer-assisted electronic devices. This is especially true in industrial, entertainment, educational, and other settings. As a medical example, many hospitals of modern day contain large arrays of electronic devices in operating rooms, interventional suites, intensive care wards, emergency rooms, laboratories, examination rooms, and/or the like. For example, glass and mercury thermometers are being replaced with electronic thermometers, intravenous drip lines now include electronic monitors and flow regulators, and traditional hand-held surgical and other medical instruments are being replaced by computer-assisted medical devices.

These computer-assisted electronic devices utilize different types of instruments and/or end effectors to perform a variety of tasks. The instruments and/or end effectors may include different designs and/or configuration to perform different tasks, procedures, and functions so as to allow an operator to manipulate objects, materials, and/or the like. As some medical examples, a surgical instrument and/or end effector may be used to perform tasks, such as cauterizing, ablating, suturing, cutting, stapling, fusing, sealing, etc., and/or combinations thereof.

Many such instruments and/or end effectors include one or more moveable elements. Each of the one or more moveable elements may be actuated so as to control a degree of freedom (DOF) of the moveable element. Examples of moveable elements include cutting blades, rotary elements, wheels, rollers, jaws, needles, catheters, stapling hammers, legs, and/or the like. For example, a cutting blade may be actuated through a trajectory or range of DOF positions to cut through a grasped material, such as tissue in a medical example. In another example, a stapling sled may be used to additionally and/or alternatively push or fire a line of staples through the grasped material.

The end effector and/or the one or more moveable elements may be applied to different types of materials with varying characteristics (e.g., depth, density, surface type, and/or the like). The material may include natural or synthetic tissues, natural rubber latex or other elastomers, metal, terrain, soil, aggregate, plastic, etc. or a combination thereof. The material surface may be generally linear, undulated, smooth, ridged, rough and/or bumpy, and/or the like. Also, different regions of the material may have similar or relatively different densities and the depth may vary as the moveable element is actuated to different DOF positions.

Consistent with the goals of a minimally invasive procedure where access to a worksite is through a workspace port, incision site, and/or the like, the moveable element on the end effector is directed to move across a trajectory to a commanded position via remote actuation. To produce movement of the moveable element via the remote actuation, various force or torque transmission components, such as gears, levers, pulleys, cables, rods, belts, bands, push coils, and/or the like, may be used to transmit force or torque from one or more inputs located at a proximal end of the instrument and along the shaft of the instrument so as to actuate the moveable element located near a distal end of the instrument. In some examples, a force or torque transmission mechanism at the proximal end of the instrument interfaces directly, or indirectly with one or more actuators, such as various motors, solenoids, servos, active actuators, hydraulics, pneumatics, and/or the like, located in a drive unit. In some examples, the drive unit may be provided on a repositionable arm and/or manipulator of a computer-assisted device, such as a patient side device or a patient side cart in a medical example.

However, elastic and plastic compression of the force or torque transmission mechanisms under load and/or other factors may create uncertainty as to the exact position of the moveable element during actuation.

Accordingly, improved techniques for the operation of end effectors with one or more moveable elements that reduce the impact of these uncertainties are desirable.

SUMMARY

Consistent with some embodiments, a computer-assisted device includes a drive system configured to actuate a moveable element to a first commanded position and a control unit coupled to the drive system. The control unit is configured to actuate, using the drive system, the moveable element to the first commanded position. The control unit is further configured to monitor a force or torque applied by the drive system to actuate the moveable element to the first commanded position, determine a force or torque limit for the drive system based on the monitored force or torque applied by the drive system in response to determining that the moveable element has reached a first position, and further actuate the moveable element to a second commanded position while limiting a force or torque applied by the drive system based on the determined force or torque limit.

Consistent with some embodiments, a method includes actuating, by a control unit of a computer-assisted device using a drive system, a moveable element to a first commanded position. The method further includes a control unit monitoring a force or torque applied by the drive system to actuate the moveable element to the first commanded position, determining a force or torque limit for the drive system based on the monitored force or torque applied by the drive system in response to determining that the moveable element has reached a first position, and further actuating the moveable element to a second commanded position while limiting a force or torque applied by the drive system based on the determined force or torque limit.

Consistent with some embodiments, a non-transitory machine-readable medium including a plurality of machine-readable instructions which when executed by one or more processors are adapted to cause the one or more processors to perform any of the methods described herein.

BRIEF DESCRIPTION OF THE DRAWINGS

FIGS. 3A-3D are simplified diagrams of an end effector according to some embodiments.

Figure 1:
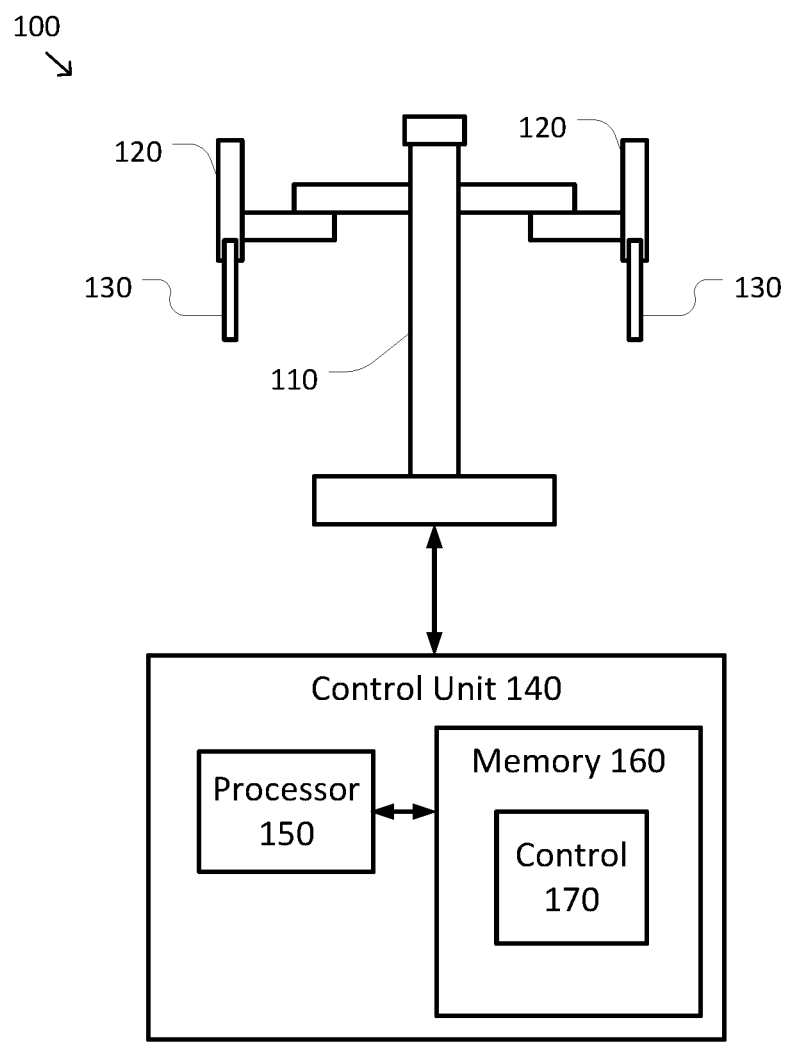
FIG. 1 is a simplified diagram of a computer-assisted system according to some embodiments.

In the figures, elements having the same designations have the same or similar functions.

DETAILED DESCRIPTION

In this description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

Further, this description's terminology is not intended to limit the invention. For example, spatially relative terms-such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of the elements or their operation in addition to the position and orientation shown in the figures. For example, if the content of one of the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. Likewise, descriptions of movement along and around various axes include various special element positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

Elements described in detail with reference to one embodiment, implementation, or module may, whenever practical, be included in other embodiments, implementations, or modules in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

In some instances, well known methods, procedures, components, and circuits have not been described in detail so as not to unnecessarily obscure aspects of the embodiments.

This disclosure describes various devices, elements, and portions of computer-assisted devices and elements in terms of their state in three-dimensional space. As used herein, the term "position" refers to the location of an element or a portion of an element in a three-dimensional space (e.g., three degrees of translational freedom along Cartesian x-, y-, and z-coordinates). As used herein, the term "orientation" refers to the rotational placement of an element or a portion of an element (three degrees of rotational freedom—e.g., roll, pitch, and yaw, angle-axis, rotation matrix, quaternion representation, and/or the like). As used herein, the term "shape" refers to a set positions or orientations measured along an element. As used herein, and for a device with repositionable arms, the term "proximal" refers to a direction toward the base of the computer-assisted device along its kinematic chain and "distal" refers to a direction away from the base along the kinematic chain. As used herein, the term "pose" refers to the six degree of freedom (DOF) spatial position and orientation of a coordinate system of interest attached to a rigid body.

Aspects of this disclosure are described in reference to computer-assisted systems and devices, which may include systems and devices that are teleoperated, remote-controlled, autonomous, semiautonomous, robotic, and/or the like. Further, aspects of this disclosure are described in terms of an implementation using a surgical system, such as the da Vinci® Surgical System commercialized by Intuitive Surgical, Inc. of Sunnyvale, Calif. Knowledgeable persons will understand, however, that inventive aspects disclosed herein may be embodied and implemented in various ways, including robotic and, if applicable, non-robotic embodiments and implementations. Implementations on da Vinci® Surgical Systems are merely exemplary and are not to be considered as limiting the scope of the inventive aspects disclosed herein. For example, techniques described with reference to surgical instruments and surgical methods may be used in other contexts. Thus, the instruments, systems, and methods described herein may be used for humans, animals, portions of human or animal anatomy, industrial systems, general robotic, or teleoperational systems. As further examples, the instruments, systems, and methods described herein may be used for non-medical purposes including industrial uses, general robotic uses, sensing or manipulating non-tissue work pieces, cosmetic improvements, imaging of human or animal anatomy, gathering data from human or animal anatomy, setting up or taking down systems, training medical or non-medical personnel, and/or the like. Additional example applications include use for procedures on tissue removed from human or animal anatomies (without return to a human or animal anatomy) and for procedures on human or animal cadavers. Further, these techniques can also be used for medical treatment or diagnosis procedures that include, or do not include, surgical aspects.

Although the following description focuses primarily on embodiments of a combined grasping, stapling, and cutting instrument, one of ordinary skill would understand that the techniques of the present disclosure may be applied to other end effectors having other types of moveable elements including both surgical and non-surgical end effectors. Examples of other types of moveable elements include rotary elements, wheels, rollers, needles, catheters, saws, scissors, moveable guides, and/or the like. Also, although the following description often discusses a computer-assisted device with repositionable arms and/or manipulators for holding and actuating the instruments and their end effectors, one of ordinary skill would understand that the methods and mechanisms of the present disclosure may also be used with computer-assisted devices that are separate from repositionable arms and/or manipulators, including devices designed to be hand-held, attached to non-repositionable fixtures, and/or the like.

FIG. 1 is a simplified diagram of a computer-assisted system 100 according to some embodiments. As shown in FIG. 1, computer-assisted system 100 includes a computer-assisted device 110 with one or more repositionable arms 120. Each of the one or more repositionable arms 120 may support one or more manipulators and/or one or more instruments 130. In some examples, computer-assisted device 110 may be consistent with a computer-assisted surgical device. The one or more repositionable arms 120 may each provide support for instruments 130 such as medical instruments, imaging devices, and/or the like. Examples of medical instruments 130 include surgical instruments for interacting with tissue, imaging or sensing devices, and/or the like. In some examples, the instruments 130 may include end effectors that are capable of, but are not limited to, performing, gripping, retracting, cauterizing, ablating, suturing, cutting, stapling, fusing, sealing, etc., and/or combinations thereof.

Computer-assisted device 110 may further be coupled to an operator workstation (not shown), which may include one or more input controls for operating the computer-assisted device 110, the one or more repositionable arms 120, and/or the instruments 130. In some examples, the one or more input controls may include master manipulators, levers, pedals, switches, keys, knobs, triggers, and/or the like. In some embodiments, computer-assisted device 110 and the operator workstation may correspond to a da Vinci® Surgical System commercialized by Intuitive Surgical, Inc. of Sunnyvale, Calif. In some embodiments, computer-assisted devices with other configurations, fewer or more repositionable arms, and/or the like may be used with computer-assisted system 100.

Computer-assisted device 110 is coupled to a control unit 140 via an interface. The interface may be wired and/or wireless, and may include one or more cables, fibers, connectors, and/or buses and may further include one or more networks with one or more network switching and/or routing devices. Operation of control unit 140 is controlled by processor 150. And although control unit 140 is shown with only one processor 150, it is understood that processor 150 may be representative of one or more central processing units, multi-core processors, microprocessors, microcontrollers, digital signal processors, field programmable gate arrays (FPGAs), application specific integrated circuits (ASICs), graphics processing units (GPUs), tensor processing units (TPUs), and/or the like in control unit 140. Control unit 140 may be implemented as a stand-alone subsystem and/or board added to a computing device or as a virtual machine. In some embodiments, control unit 140 may be included as part of the operator workstation and/or operated separately from, but in coordination with the operator workstation.

Memory 160 may be used to store software executed by control unit 140 and/or one or more data structures used during operation of control unit 140. Memory 160 may include one or more types of machine-readable media. Some common forms of machine-readable media may include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

As shown in FIG. 1, memory 160 includes a control module 170 that may be used to support autonomous, semiautonomous, and/or teleoperated control of computer-assisted device 110. Control module 170 may include one or more application programming interfaces (APIs) for receiving position, motion, force, torque, and/or other sensor information from computer-assisted device 110, repositionable arms 120, and/or instruments 130, exchanging position, motion, force, torque, and/or collision avoidance information with other control units regarding other devices, and/or planning and/or assisting in the planning of motion for computer-assisted device 110, repositionable arms 120, and/or instruments 130. In some examples, control module 170 further supports autonomous, semiautonomous, and/or teleoperated control of the instruments 130 during the performance of various tasks. And although control module 170 is depicted as a software application, control module 170 may optionally be implemented using hardware, software, and/or a combination of hardware and software.

In some embodiments, computer-assisted system 100 may be found in an operating room and/or an interventional suite. And although computer-assisted system 100 includes only one computer-assisted device 110 with two repositionable arms 120 and corresponding instruments 130, one of ordinary skill would understand that computer-assisted system 100 may include any number of computer-assisted devices with repositionable arms and/or instruments of similar and/or different in design from computer-assisted device 110. In some examples, each of the computer-assisted devices may include fewer or more repositionable arms and/or instruments.

Figure 2:
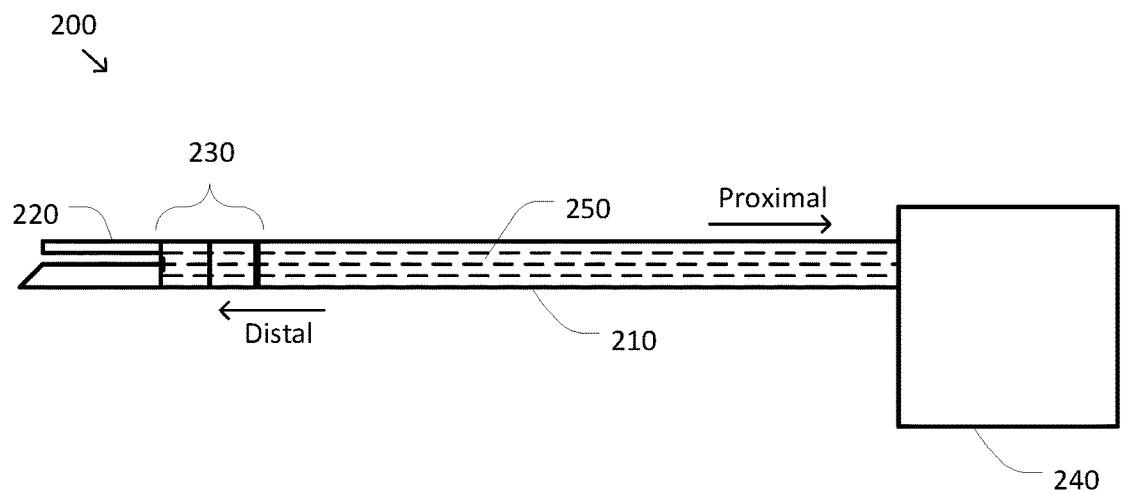
FIG. 2 is a simplified diagram showing an instrument according to some embodiments.

FIG. 2 is a simplified diagram showing an instrument 200 according to some embodiments. In some embodiments, instrument 200 may be consistent with any of the instruments 130 of FIG. 1. The directions "proximal" and "distal" as depicted in FIG. 2 and as used herein help describe the relative orientation and location of components of instrument 200. Distal generally refers to elements in a direction further along a kinematic chain from a user or machine holding the instrument 200, a base of a computer-assisted device for holding the instrument 200, such as computer-assisted device 110, and/or or closest to a worksite in the intended operational use of instrument 200. Proximal generally refers to elements in a direction closer along a kinematic chain toward the base of the computer-assisted device, a user or machine holding the instrument 200, and/or one of the repositionable arms or manipulators of the computer-assisted device for holding the instrument 200.

As shown in FIG. 2, instrument 200 includes a shaft 210 coupling an end effector 220 located at a distal end of shaft 210 to where the instrument 200 is mounted to a repositionable arm, a manipulator, and/or a computer-assisted device at a proximal end of shaft 210. Depending upon the particular procedure for which the instrument 200 is being used, shaft 210 may be inserted through an opening into a workspace, such as an access port and/or an opening in a patient (e.g., a body wall incision, a natural orifice, and/or the like) in order to place end effector 220 in proximity to a remote worksite located within the workspace. As further shown in FIG. 2, end effector 220 is generally consistent with a two jawed gripper-style end effector, which in some embodiments may further include a cutting and/or a stapling mechanism as is described in further detail below with respect to FIGS. 3A-3D. However, it is understood that different instruments 200 with different end effectors 220, such as end effectors with fasteners other than staples and/or for performing different tasks, are possible and may be consistent with the embodiments of instrument 200.

An instrument, such as instrument 200 with end effector 220 typically uses multiple DOFs during its operation. In some examples, one or more of the DOFs may correspond to a position of a corresponding moveable element. Depending upon the configuration of instrument 200 and the repositionable arm, manipulator, and/or computer-assisted device to which it is mounted, various DOFs that may be used to position, orient, and/or operate end effector 220 are possible. In some examples, shaft 210 may be inserted in a distal direction and/or retreated in a proximal direction to provide an insertion DOF that may be used to control how deep within the workspace or worksite that end effector 220 is placed. In some examples, shaft 210 may be able rotate about its longitudinal axis to provide a roll DOF that may be used to rotate end effector 220. In some examples, additional flexibility in the position and/or orientation of end effector 220 may be provided by one or more joints and/or links, such as the joints and links of a repositionable arm 120, located proximal to shaft 210 and instrument 200. In some examples, an optional articulated wrist 230 may be used to couple end effector 220 to the distal end of shaft 210. In some examples, articulated wrist 230 may optionally include one or more rotational joints, such as one or more roll, pitch or yaw joints that may provide one or more "roll," "pitch," and "yaw" DOF(s), respectively, that may be used to control an orientation of end effector 220 relative to the longitudinal axis of shaft 210. In some examples, the one or more rotational joints may include a pitch and a yaw joint; a roll, a pitch, and a yaw joint, and/or the like. In some examples, end effector 220 further includes a grip DOF used to control the opening and closing of the jaws of end effector 220 and/or an activation DOF used to control the extension, retraction, and/or operation of a stapling and cutting mechanism as is described in further detail below.

Instrument 200 further includes a drive system 240 located at the proximal end of shaft 210. And although drive system 240 is shown as part of instrument 200, one or more portions of drive system 240 may be part of a device, a manipulator, and/or a repositionable arm to which instrument is mounted. Drive system 240 includes one or more components for introducing forces and/or torques to instrument 200 that can be used to manipulate the various DOFs supported by instrument 200. In some examples, drive system 240 may optionally include one or more motors, solenoids, servos, active actuators, hydraulics, pneumatics, and/or the like and/or be coupled to one or more motors, solenoids, servos, active actuators, hydraulics, pneumatics, and/or the like of a manipulator and/or repositionable arm to which instrument 200 and/or drive system 240 are mounted. The one or more motors, solenoids, servos, active actuators, hydraulics, pneumatics, and/or the like are operated based on signals received from a control unit, such as control unit 140 of FIG. 1. In some examples, the signals may include one or more currents, voltages, pulse-width modulated wave forms, and/or the like. In some examples, drive system 240 may optionally include one or more shafts, gears, pulleys, rods, bands, push coils, and/or the like which may be coupled to corresponding motors, solenoids, servos, active actuators, hydraulics, pneumatics, and/or the like. In some examples, the one or more drive inputs, such as shafts, gears, pulleys, rods, bands, push coils, and/or the like, are used to receive forces and/or torques from the motors, solenoids, servos, active actuators, hydraulics, pneumatics, and/or the like and apply those forces and/or torques to adjust the various DOFs of surgical instrument 200. In this discussion, both "force" and "torque" are sometimes used individually to indicate linear force, rotational torque, and/or both, as applicable.

In some embodiments, the forces and/or torques generated by and/or received by drive system 240 are transferred from drive system 240 and along shaft 210 to the various joints and/or elements of instrument 200 located distal to drive system 240 using one or more force or torque transmission mechanisms 250. In some examples, the one or more force or torque transmission mechanisms 250 may optionally include one or more gears, levers, pulleys, cables, rods, bands, push coils, and/or the like. In some examples, shaft 210 is hollow and the force or torque transmission mechanisms 250 pass along the inside of shaft 210 from drive system 240 to the corresponding DOFs in end effector 220 and/or articulated wrist 230. In some examples, each of the force or torque transmission mechanisms 250 may optionally be a cable disposed inside a hollow sheath or lumen in a Bowden cable like configuration. In some examples, the cable and/or the inside of the lumen may optionally be coated with a low-friction coating such as polytetrafluoroethylene (PTFE) and/or the like. In some examples, as the proximal end of each of the cables is pulled and/or pushed inside drive system 240, such as by wrapping and/or unwrapping the cable about a capstan or shaft, the distal end of the cable moves accordingly and applies a suitable force and/or torque to adjust one or more of the DOFs of end effector 220, articulated wrist 230, and/or instrument 200.

FIGS. 3A-3D are simplified diagrams of an end effector 300 according to some embodiments. In some embodiments, end effector 300 is consistent with end effector 220. As shown in FIGS. 3A-3D, end effector 300 includes a mechanism for jaw closure, material (e.g., tissue in a medical example) stapling, and material cutting. And although end effector 300 is shown and described with one fixed and one moveable jaw, it is understood that end effector 300 could be modified to use two moveable jaws. It should be further understood that although the description below is in the context of a grasping, stapling, and cutting instrument that simultaneously grasps, staples, and cuts material, the aspects so described may be applicable to instruments with or without cutting features, instruments supporting fusing rather than stapling, instruments performing other tasks, and/or the like.

FIG. 3A shows a cut-way side view of end effector 300 prior to actuation so that the jaws of end effector 300 are shown in an open position. As shown, end effector 300 includes a first jaw 310 that is generally fixed. Jaw 310 is designed to receive a replaceable staple cartridge 320 holding a plurality of staples 330 and a plurality of staple pushers 335. Staple cartridge 320 is designed to be replaceable so that end effector 300 is reusable by removing a first staple cartridge 320 after one or more of the staples 330 are used and replacing it with a second staple cartridge 320 having a new set of staples 330 that can be used to perform further stapling tasks. FIG. 3B shows a top view of staple cartridge 320. As depicted in FIG. 3B, staple cartridge includes six rows of staple slots 340 through which staples 330 may be applied to a grasped material upon actuation of end effector 300. The rows of staple slots 340 include three rows on each side of a cutting slot 350, which is described in further detail below. Placing staples 330 on both sides of cutting slot 350 allows for the application of staples 330 to both sides of a desired cutting line so as to close the material on both sides of the cutting line. The rows of staple slots 340 are also offset relative to each other to provide more complete material closure along both sides of the cutting line. And although, staple cartridge 320 is shown with six rows of offset staple slots 340, each having six staple slots 340 of uniform size, it is understood that fewer or more rows of staple slots with fewer or more staples, staple slots of varying size, and staple slots of varying patterns are possible.

As further shown in FIG. 3A, end effector 300 further includes a second jaw 360 that is moveable about a pivot point (not shown) near its proximal end. In the context of a stapling instrument, second jaw 360 may alternatively be referred to as anvil 360. In the embodiments shown in FIG. 3A, anvil 360 includes a transitional edge 370 configured so that upon initial actuation of end effector 300, a gap between anvil 360 and jaw 310 is rapidly reduced until a material is grasped between anvil 360 and jaw 310. Actuation of end effector 300 is accomplished by movement of a reciprocating element 380 from the proximal end of end effector 300 to the distal end of end effector 300. Reciprocating element 380 is coupled to the distal end of one or more of the force or torque transmission mechanisms, such as one or more of force or torque transmission mechanisms 250.

Reciprocating element 380 includes a sled 382 and a flange 384 with a cutting blade 386 coupled between the sled 382 and flange 384. Reciprocating element 380 has a general I-beam style cross-sectional shape as shown in the cut-away end view of end effector 300 shown in FIG. 3D. As end effector 300 is actuated for stapling, sled 382 is propelled along within jaw 310 and staple cartridge 320 as reciprocating element 380 is pushed by force or torque transmission mechanism 250. Sled 382 includes a wedge-shaped leading or distal end such that, as the leading end encounters each of the staple pushers 335, the leading end pushes the staple pushers 335 against corresponding staples 330. This action results in the firing of each of the staples 330 through a respective one of the staple slots 340. Although sled 382 is shown with a single wedge at its leading edge, sled 382 may optionally include separate wedges for each of the rows of staples 330 and staple pushers 335 in staple cartridge 320. Additionally, each of the separate wedges may optionally be staggered relative to each other in the direction of sled 382 movement. In some embodiments, staple pushers 335 are optional and the leading edge of sled 382 pushes directly against staples 330. As sled 382 is being propelled along within jaw 310 and staple cartridge 320, flange 384 is propelled along within anvil 360. As the leading distal end of flange 384 encounters transitional edge 370, flange 384 causes initial rapid closure of the gap between anvil 360 and jaw 310. Cutting blade 386 is located somewhat proximally to the distal ends of sled 382 and flange 384 so that cutting of any grasped material trails the firing of the staples 330 along both sides of the cutting line. As reciprocating element 380 is actuated, cutting blade 386 travels along cutting slot 350 as well as a corresponding cutting slot 355 located in anvil 360.

FIGS. 3C and 3D show a cut-away side and a cut-away end view, respectively, of end effector 300 after it has been fully actuated. As shown, reciprocating element 380, along with sled 382, flange 384, and cutting blade 386, is located at the distal end of end effector 300. As the leading edge of sled 382 encounters each of the staple pushers 335, it pushes the staple pushers 335 which in turn push the staples 330 up through respective staple slots 340 where they are pressed through any grasped material into a face of anvil 360 where they are bent into final shape as shown in FIG. 3C. The gap between anvil 360 and jaw 310 is maintained by the presence of flange 384 within anvil 360. In this way, reciprocating element 380, sled 382, flange 384, and cutting blade 386 are all components of end effector 300 which move in response to applied force or torque provided by the one or more actuators controlling movement of reciprocating element 380.

Operation of end effector 300 is subject to several practical considerations as it is actuated. In some examples, end effector 300 may be used with different types of materials with varying characteristics (e.g., depth, density, surface type, and/or the like). In some examples, the materials may include natural or synthetic tissues, natural rubber latex or other elastomers, metal, terrain, soil, aggregate, plastic, etc. or a combination thereof. In some examples, the material surface may be generally linear, undulated, smooth, ridged, rough and/or bumpy, etc. In some examples, different areas of the material may have similar or relatively different densities and the depth may vary through the trajectory. As a result of the variations in the materials, the amount of force or torque that is applied to actuate sled 382 and/or cutting blade 386 may vary as different portions of the material are stapled and/or cut.

In some examples, sled 382, cutting blade 386, the one or more force or torque transmission mechanisms coupling sled 382 and/or cutting blade 386 to the one or more actuators, and/or the one or more actuators may vary somewhat from instrument to instrument and device to device, may have frictional and/or inertial properties that vary based on DOF position, and/or the like. In some examples, elastic and/or plastic compression and/or the like may occur when sled 382, cutting blade, the one or more force or torque transmission mechanisms, and/or the one or more actuators are actuated to change the position of sled 382 and/or cutting blade 386 and/or when sled 382, cutting blade, the one or more force or torque transmission mechanisms, and/or the one or more actuators are placed under load.

In some examples, direct monitoring of the sled may not be possible or practical is there may be insufficient space in end effector 300 to include one or more sensors to monitor the position of sled 382 and/or cutting blade 386 and/or sled 382 and/or cutting blade 386 may not be detectable in images of end effector 300 due to occlusion by other portions of end effector 300, the grasped material, and/or other objects near the worksite. In these cases, the position of the sled 382 and/or cutting blade 386 may be inferred by monitoring positions of the one or more actuators used to actuate sled 382 and/or cutting blade 386. However, the position of sled 382 and/or cutting blade 386 tends to lag somewhat behind the one or more actuators due to the compression in sled 382, cutting blade 386, and/or the one or more force or torque transmission mechanisms.

In some examples, the uncertainty in the actual position of sled 382 and/or cutting blade 386 may impact the ability to use end effector 300 in a reliable manner. For example, it is generally desirable to operate sled 382 and/or cutting blade 386 so that actuation of sled 382 and/or cutting blade 386 moves the DOF associated with sled 382 and/or cutting blade 386 through a complete range of motion to a maximum distal position or hard stop position. In some examples, a failure to move the DOF to the maximum distal position may result in one or more partially formed staples, incomplete cutting of the material, and/or the like. Accordingly, it is often desirable to actuate sled 382 and/or cutting blade 386 in such a way to ensure that sled 382 and/or cutting blade 386 reach the maximum distal position. In some embodiments, other types of DOFs may be operated with similar goals. Some non-limiting examples of these other types of DOFs may include retracting sled 382 and/or cutting blade 386 back to a parked position after use, operating jaw 360 to a fully open or fully closed position, extending a needle or biopsy probe to a fully extended position, and/or the like.

One possible solution to this problem is to deliberately actuate a DOF past its maximum or hard stop position. In some examples, this may be accomplished by actuating the DOF subject to a commanded position along a positional trajectory and/or to commanded position corresponding to a position setpoint that is sufficiently beyond the maximum position to guarantee that the DOF reaches the maximum position despite the variations in the end effector, the one or more force or torque transmissions mechanisms, the one or more actuators, the variations in a material being manipulated, loading on the end effector, compression in the apparatus, and/or the like. In some examples, the commanded positions of the positional trajectory and/or the positional setpoint may be selected based on a worst case estimate of how much the DOF may lag behind the one or more actuators when the DOF reaches the maximum position. In some examples, an additional safety margin may also be added. And while this helps ensure that the DOF reaches the maximum position, operation of the DOF in this fashion may result in undesirable outcomes. In some examples, attempting to operate the DOF past the maximum position may put unneeded stress on the end effector, the one or more force or torque transmission mechanisms, and/or the one or more actuators. This may cause damage to the end effector, the one or more force or torque transmission mechanisms, and/or the one or more actuators and/or reduce their operational lifetime. In some examples, this may be compensated for somewhat by using stronger or larger materials in the end effector, the one or more force or torque transmission mechanisms, and/or the one or more actuators, but this may increase the size, weight, and cost of the instrument and may reduce its usefulness for some tasks. In some examples, when the DOF reaches the maximum position and runs into a hard stop feature (e.g., a distal end of jaw 310 and/or jaw 360 in the examples of sled 382 and/or cutting blade 386), the impact may cause the end effector to jerk or twitch, which may cause damage to the end effector, put additional strain on a grasped material, and/or the like.

Accordingly, it is desirable to have techniques that help ensure that a DOF can be actuated to reach a maximum position while avoiding the side effects caused by running into a hard stop feature with excessive force.

Figure 4:
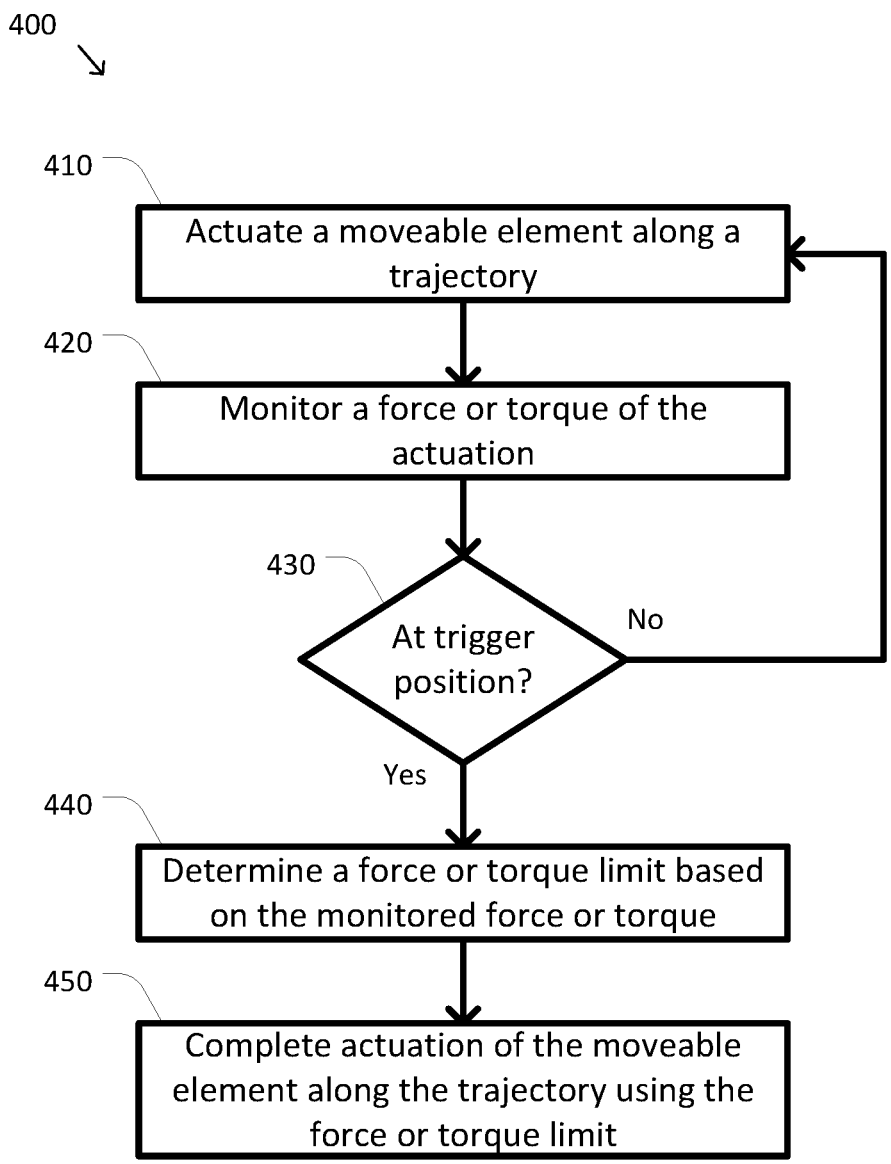
FIG. 4 is a simplified diagram of a method for controlling a moveable element of an end effector according to some embodiments.

FIG. 4 is a simplified diagram of a method for controlling a moveable element of an end effector according to some embodiments. One or more of the processes 410-450 of method 400 may be implemented, at least in part, in the form of executable code stored on non-transient, tangible, machine-readable media. This executable code, when run by one or more processors (e.g., the processor 150 in control unit 140), may cause the one or more processors to perform one or more of the processes 410-450. In some embodiments, method 400 may be performed by a module, such as control module 170. In some embodiments, method 400 may be used to control the actuation of a moveable element in such a way to ensure that the moveable element reaches a maximum or hard stop position while reducing the undesired effects caused by running the moveable element into a hard stop feature. In some embodiments, processes 410 and 420 may be performed concurrently.

Figure 5:
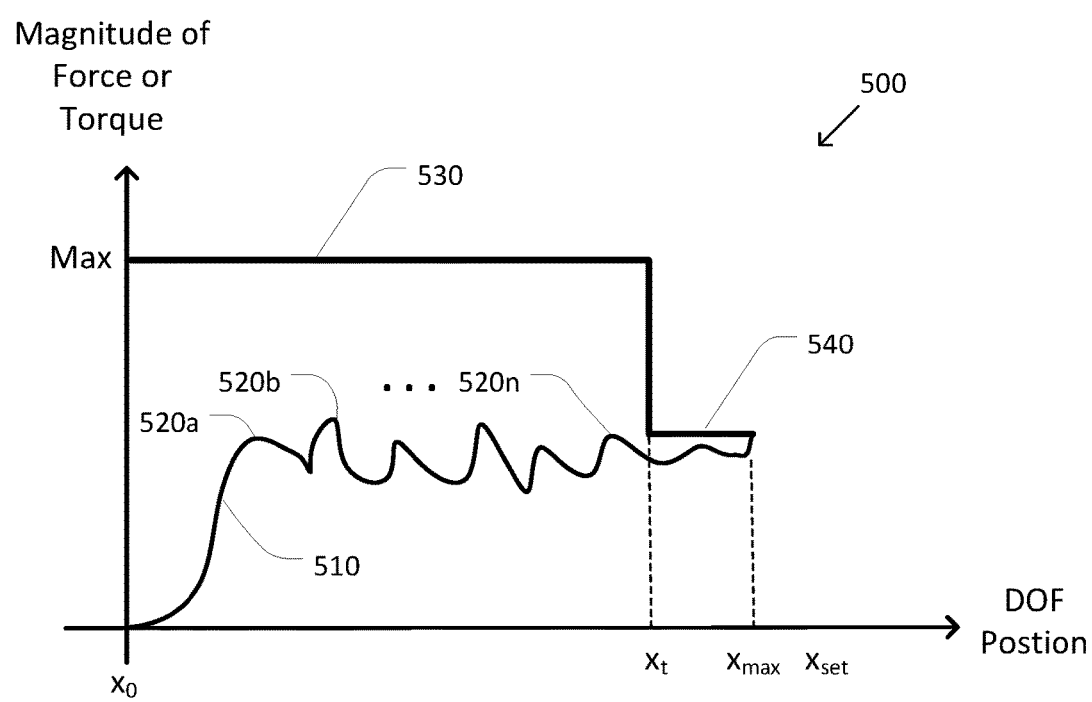
FIG. 5 is a simplified diagram of force or torque associated with a moveable element according to some embodiments.

Aspects of method 400 are described via reference to FIG. 5, which is a simplified diagram of force or torque associated with a moveable element according to some embodiments. However, it is understood that examples of FIG. 5 are non-limiting and that other values, shapes, behaviors, and/or the like depicted in FIG. 5 may be different for different end effectors, different moveable elements, different DOFs, different tasks, and/or the like. FIG. 5 includes various curves showing changes in forces and/or torques and/or forces and/or torque limits as a moveable element is actuated to various DOF positions.

At a process 410, a moveable element is actuated along a trajectory. In some examples, the moveable element may be any moveable element of an end effector, such as sled 382, cutting blade 386, and/or jaw 360 of end effector 300. The moveable element is actuated by causing an actuator, such as an actuator in drive system 240 and/or coupled to drive system 240, to apply a force or torque that is used to control a DOF corresponding to the moveable element. In some examples, the actuator is controlled by sending one or more signals, such as a current, a voltage, a pulse-width modulated signal, and/or the like to the actuator. The actual effects of the actuation of the moveable element depend on the design, use, and purpose of the moveable.

In some examples, actuation of the moveable element includes providing a trajectory of commanded positions or position setpoints for the moveable element that are iteratively applied to a position control loop over time to move the moveable element through a range of motion from a starting position, such as position xo of FIG. 5, to reach a maximum position, such as position $x_{max}$ of FIG. 5. In some examples, the trajectory may include setpoints that are equally spaced and/or variably spaced as makes sense for the task being performed. In some examples, the setpoints may be applied to the position control loop at regular time intervals, irregular time intervals, or as interim goal positions are reached by the moveable element. In some examples, one or more of the position setpoints are located past the maximum position $x_{max}$, such as at position $x_{set}$ of FIG. 5, to help ensure that the moveable element reaches the maximum position $x_{max}$. In some examples, the trajectory may include only a single setpoint corresponding to $x_{set}$. In some examples, $x_{set}$ may be positioned sufficiently past the maximum position $x_{max}$ to ensure that the moveable element will reach the maximum position $x_{max}$.

As the moveable element is being actuated by process 410, a magnitude of the maximum force or torque that may be applied by the actuator to actuate the moveable element is set to a maximum value, such as is indicated by the maximum force or torque limit 530 in FIG. 5. In some examples, the maximum force or torque limit 530 may be selected based on a type or model of the end effector, a type or model of the instrument, a type or model of the actuator, a type or model of the manipulator or repositionable arm to which the instrument is mounted, a task being performed, a type of material being manipulated, operator preference, and/or the like.

At a process 420, a force or torque of the actuation is monitored. Using one or more sensors and/or control algorithms, the force or torque being applied by the actuator is monitored as the moveable element is moved along the trajectory using process 410. In some examples, the force or torque of the actuation may be monitored at the actuator, where the actuator is coupled to one or more force or torque transmission mechanisms, at a point along the kinematic chain between the actuator and the moveable element, and/or the like. For example, when the actuator is a motor, current applied to the motor may be monitored and used to determine a torque being applied by the motor. In some examples, the monitored force or torque may correspond to a magnitude of the force or torque being applied by the actuator. Referring to the examples of FIG. 5, applied force or torque curve 510 corresponds to the magnitude of the force or torque of the actuation as the moveable element moves between starting position xo and maximum position $x_{max}$.

In some examples and as shown by force or torque curve 510, the magnitude of the force or torque of the actuation tends to vary as the moveable element is actuated. In some examples, the magnitude of the force or torque of the actuation may vary due to variations in a material being worked on. In some examples, the variations in material may include one or more of thickness of the material, a density of the material, a toughness of the material, one or more surface properties of the material (e.g., texture, friction, shape, and/or the like), a shape of the material, changes in a type of the material, and/or the like. In some examples, the magnitude of the force or torque of the actuation may vary due to variations in the actuator, the one or more force or torque transmission mechanisms, the end effector, the moveable element, and/or the like, such as different operating characteristics at different positions of the moveable element. In some examples, the magnitude of the force or torque of the actuation may vary due to a secondary task being performed as the moveable element is actuated, such as the firing of one or more staples through the material.

In some examples, the force or torque of the actuation may be continuously monitored and/or periodically sampled. In some examples, the sampling may occur at regular intervals, such as with every pass through a control cycle of the actuation. In some examples, the sampling may occur when the moveable element reaches particular positions, such as positions at regular intervals, positions corresponding to the setpoints of the trajectory, and/or the like. In some examples, the values of the force or torque of the actuation may be low pass filtered to reduce the effects of noise, vibrations, and/or the like.

In some examples, a magnitude of the force or torque of the actuation may be monitored to detect one or more local maxima in the magnitude of the force or torque of the actuation, such as identified by local maxima 520a-520n of FIG. 5. In some examples, a local maxima in the magnitude of the force or torque of the actuation may be detected whenever it is noted that three consecutive values for the magnitude of the force or torque of the actuation have an increase between the first two values and a decrease between the last two values. In some examples, a local maxima in the magnitude of the force or torque of the actuation may be detected by continuing to record a largest observed magnitude in the force or torque of the actuation until an observed magnitude of the force or torque of the actuation is a configurable offset below the largest observed magnitude of the force or torque of the actuation. When the observed magnitude of the force or torque of the actuation is below the largest observed magnitude of the force or torque of the actuation by the configurable offset, the largest observed magnitude of the force or torque of the actuation is recorded as a new local maximum and the largest observed magnitude of the force or torque of the actuation is reset to zero. In some examples, the configurable offset may be determined based on one or more of a percentage of the largest observed magnitude of the force or torque of the actuation, a type or model of the actuator, a type or model of the manipulator or repositionable arm to which the instrument is mounted, a task being performed, a type of material being manipulated, operator preference, a velocity of the moveable element, and/or the like. In some examples, one or more of the local maxima are recorded.

At a process 430, it is determined whether the moveable element has reached a trigger position, such as position $x_t$ in FIG. 5. Using one or more sensors, a position of the actuator and/or a position of a detectable location on the moveable element is monitored. For example, the sensors may measure a rotation angle of a drive shaft of the actuator. In some examples, the one or more sensors may include a shaft encoder, Hall Effect sensor, and/or the like. In some examples, the position of the moveable element may be an estimate of the actual position of the moveable element.

In some examples, the trigger position $x_t$ may be set to a fixed distance before the maximum position $x_{max}$. In some examples, the trigger position $x_t$ may be set a fixed percentage (e.g., 65-85 percent) of the distance between the starting positions xo and the maximum position $x_{max}$. In some examples, the trigger position $x_t$ may be adjusted based on one or more of a type or model of the actuator, a type or model of the manipulator or repositionable arm to which the instrument is mounted, a task being performed, a type of material being manipulated, operator preference, a velocity of the moveable element, and/or the like. In some examples, the velocity of the moveable element may be determined based on a change in the position of the moveable element, a numerical differentiation technique (e.g., using finite differences), and/or the like.

When the position of the moveable element has reached the trigger position $x_t$, a new force or torque limit for the actuation of the moveable element is determined using a process 440. When the moveable element has not reached the trigger position $x_t$ actuation of the moveable element continues by repeating processes 410 and 420.

At process 440, a force or torque limit is determined based on the monitored force or torque. In some examples, the determined force or torque limit is determined to provide an upper limit on a magnitude of the force or torque that may be applied by the actuator to further actuate the moveable element and may correspond to a force or torque magnitude limit. The force or torque limit is selected to reduce the amount of force that may occur when the moveable element runs into a hard stop feature. In some examples, the force or torque limit is selected based on the monitoring of the force or torque of the actuation performed during process 420. In some examples, the force or torque limit is selected based on one or more of the local maxima of the magnitude of the force or torque of the actuation. In some examples, the local maxima provide a good indication of a minimum magnitude in an amount of force or torque that may be needed to actuate the moveable element to the maximum position $x_{max}$.

In some examples, one of the local maxima, such as a most recently recorded local maximum (e.g., local maximum 520n as shown in FIG. 5, which results in the force or torque limit being set to value 540) is selected as the force or torque limit. In some examples, a largest local maximum (e.g., a global maximum) of the magnitude of the force or torque of the actuation is selected as the force or torque limit. In some examples, an aggregation of one or more of the local maxima is selected as the force or torque limit. In some examples, the aggregation may include averaging all of the local maxima, averaging a configurable number of the most recent local maxima, exponential smoothing of each of the local maxima, and/or the like. In some examples, an offset may be added to the force or torque limit to provide an extra margin to ensure the moveable element can reach the maximum position $x_{max}$. In some examples, the offset may be a configurable amount, such as a configurable percentage of the maximum force or torque limit 530 or a configurable percentage of the force or torque limit determined from the one or more local maxima. In some examples, the offset may be determined based on one or more of a type or model of the actuator, a type or model of the manipulator or repositionable arm to which the instrument is mounted, a task being performed, a type of material being manipulated, operator preference, a velocity of the moveable element, and/or the like.

At a process 450, actuation of the moveable element along the trajectory is completed using the determined force or torque limit. Actuation of the moveable element during process 450 is substantially similar to the actuation of process 450 except that the magnitude of the force or torque that may be applied to actuate the moveable element, is limited to the force or torque magnitude limit determined during process 440. In this way, when the moveable element does run into the hard stop feature as it is actuated toward $x_{set}$, the amount of force is reduced to a reasonable practical minimum that may reduce wear and tear, jerking of the end effector, and/or the like.

In some examples, continued monitoring of the force or torque of the actuation may detect when the moveable element reaches the maximum position $x_{max}$. In some examples, when a magnitude of the force or torque of the actuation reaches the force or torque limit determined during process 440, this indicates that the moveable element has reached the maximum position $x_{max}$. In some examples, further actuation to change a position of the moveable element may be stopped at this point by setting the commanded position or position setpoint for the moveable element to the current position of the moveable element.

As discussed above and further emphasized here, FIG. 4 is merely an example which should not unduly limit the scope of the claims. One of ordinary skill in the art would recognize many variations, alternatives, and modifications. In some embodiments, when more than one actuator is used to actuate the moveable element, the force or torque of each of the actuators may be monitored separately to determine a separate force or torque limit for each actuator use during its version of process 450 and/or an aggregation of the force or torque of the actuation of two or more of the actuators may be used to set an aggregate force or torque limit that is applied to two or more of the actuators.

In some embodiments, method 400 may be repeated for each trajectory of the moveable element. In some embodiments, monitoring of the force or torque of the actuation and/or the recording of local maxima may be reset and/or started anew each time the moveable element is stopped or stalled. In some examples, the moveable element may be stopped or stalled when its speed remains below a configurable threshold for a configurable period of time.

Some examples of control units, such as control unit 140 may include non-transient, tangible, machine-readable media that include executable code that when run by one or more processors (e.g., processor 150) may cause the one or more processors to perform the processes of method 400. Some common forms of machine-readable media that may include the processes of method 400 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A computer-assisted device comprising:
a drive system configured to actuate a moveable element to a first commanded position; and
a control unit coupled to the drive system;
wherein the control unit is configured to:
actuate, using the drive system, the moveable element to the first commanded position;
monitor a force or torque applied by the drive system to actuate the moveable element toward the first commanded position;
determine that the moveable element has reached a predefined trigger position;
in response to determining that the moveable element has reached the predefined trigger position, determine a force or torque limit to be applied during further actuation of the moveable element based on the monitored force or torque applied by the drive system; and
further actuate the moveable element to a second commanded position while limiting a force or torque applied by the drive system to the determined force or torque limit.

2. The computer-assisted device of claim 1, wherein the computer-assisted device is a medical device.

3. The computer-assisted device of claim 1, wherein the moveable element comprises a cutting blade for cutting a grasped material or a stapling sled for pushing one or more staples through the grasped material.

4. The computer-assisted device of claim 1, wherein the force or torque limit corresponds to a limit in a magnitude of the force or torque applied by the drive system.

5. The computer-assisted device of claim 1, wherein the second commanded position is selected to actuate the moveable element past a maximum position for the moveable element.

6. The computer-assisted device of claim 1, wherein the first and second commanded positions are included in a plurality of commanded positions in a trajectory for moving the moveable element through a range of motion.

7. The computer-assisted device of claim 1, wherein the predefined trigger position is located a first distance before a maximum position of the moveable element.

8. The computer-assisted device of claim 7, wherein the first distance is determined based on a velocity of the moveable element.

9. The computer-assisted device of claim 1, wherein the control unit is configured to determine the force or torque limit based on one or more local maxima in a magnitude of the monitored force or torque applied by the drive system to actuate the moveable element.

10. The computer-assisted device of claim 9, wherein the one or more local maxima consists of:
  a last local maximum in the monitored force or torque applied by the drive system to actuate the moveable element before the moveable element has reached the predefined trigger position; or
  a global maximum in the monitored force or torque.

11. The computer-assisted device of claim 9, wherein the control unit is configured to determine the force or torque limit based on an aggregation of the one or more local maxima.

12. The computer-assisted device of claim 1, wherein the control unit is further configured to add an offset to the force or torque limit.

13. The computer-assisted device of claim 1, wherein the control unit is configured to determine that the moveable element has reached a maximum position when the force or torque applied by the drive system reaches the force or torque limit.

14. A method comprising:
  actuating, by a control unit of a computer-assisted device using a drive system, a moveable element toward a first commanded position;
  monitoring, by the control unit, a force or torque applied by the drive system to actuate the moveable element toward the first commanded position;
  determining that the moveable element has reached a predefined trigger position;
  in response to determining that the moveable element has reached the predefined trigger position, determining, by the control unit, a force or torque limit to be applied during further actuation of the moveable element based on the monitored force or torque applied by the drive system; and
  further actuating, by the control unit, the moveable element to a second commanded position while limiting a force or torque applied by the drive system to the determined force or torque limit.

15. The method of claim 14, wherein the force or torque limit corresponds to a limit in a magnitude of the force or torque applied by the drive system.

16. The method of claim 14, wherein the second commanded position is selected to actuate the moveable element past a maximum position for the moveable element.

17. The method of claim 14, further comprising determining the force or torque limit based on one or more local maxima in a magnitude of the monitored force or torque applied by the drive system to actuate the moveable element.

18. A non-transitory machine-readable medium comprising a plurality of machine-readable instructions which when executed by one or more processors associated with a computer-assisted device are adapted to cause the one or more processors to perform a method comprising:
  actuating, using a drive system, a moveable element toward a first commanded position;
  monitoring a force or torque applied by the drive system to actuate the moveable element to the first commanded position;
  determining that the moveable element has reached a predefined trigger position;
  in response to determining that the moveable element has reached the predefined trigger position, determining a force or torque limit to be applied during further actuation of the moveable element based on the monitored force or torque applied by the drive system; and
  further actuating the moveable element to a second commanded position while limiting a force or torque applied by the drive system to the determined force or torque limit.

19. The non-transitory machine-readable medium of claim 18, wherein:
  the predefined trigger position is located a first distance before a maximum position of the moveable element; and
  the method further comprises determining the first distance based on a velocity of the moveable element.

20. The non-transitory machine-readable medium of claim 18, wherein the method further comprises determining the force or torque limit based on one or more local maxima in a magnitude of the monitored force or torque applied by the drive system to actuate the moveable element.

* * * * *